US012753246B2

(12) United States Patent
Naito et al.

(10) Patent No.: US 12,753,246 B2
(45) Date of Patent: Oct. 6, 2026

(54) CELLULOSE ACETATE PARTICLES

(71) Applicant: FUJIFILM Business Innovation Corp., Tokyo (JP)

(72) Inventors: Ayu Naito, Kanagawa (JP); Kazusei Yoshida, Kanagawa (JP); Takeshi Iwanaga, Kanagawa (JP); Kenji Yao, Kanagawa (JP); Tetsuya Taguchi, Kanagawa (JP); Hirokazu Hamano, Kanagawa (JP)

(73) Assignee: FUJIFILM Business Innovation Corp., Tokyo (JP)

( * ) Notice: Subject to any disclaimer, the term of this patent is extended or adjusted under 35 U.S.C. 154(b) by 338 days.

(21) Appl. No.: 18/458,986

(22) Filed: Aug. 30, 2023

(65) Prior Publication Data

US 2024/0327545 A1 Oct. 3, 2024

(30) Foreign Application Priority Data

Mar. 28, 2023 (JP) ................................ 2023-052436

(51) Int. Cl.

| | |
|---|---|
| ***C08B 3/06*** | (2006.01) |
| ***A61K 8/73*** | (2006.01) |
| ***A61Q 1/00*** | (2006.01) |
| ***A61Q 1/06*** | (2006.01) |
| ***A61Q 1/10*** | (2006.01) |
| ***A61Q 17/04*** | (2006.01) |
| ***A61Q 19/00*** | (2006.01) |

(52) U.S. Cl.

CPC ................ *C08B 3/06* (2013.01); *A61K 8/731* (2013.01); *A61Q 1/00* (2013.01); *A61Q 1/06* (2013.01); *A61Q 1/10* (2013.01); *A61Q 17/04* (2013.01); *A61Q 19/00* (2013.01)

(58) Field of Classification Search

CPC .. C08B 3/06; A61K 8/731; A61Q 1/00; A61Q 1/06; A61Q 1/10; A61Q 17/04; A61Q 19/00; C08L 1/12

See application file for complete search history.

(56) References Cited

U.S. PATENT DOCUMENTS

| | | | | |
|---|---|---|---|---|
| 4,888,420 | A | 12/1989 | Steiner et al. | |
| 9,096,690 | B2 | 8/2015 | Shiomi et al. | |
| 9,341,622 | B2 | 5/2016 | Shiomi et al. | |
| 2016/0032020 | A1 * | 2/2016 | Ukita | C08B 3/28 536/76 |
| 2020/0179261 | A1 * | 6/2020 | Kobayashi | A61K 8/36 |
| 2022/0142900 | A1 * | 5/2022 | Kobayashi | C08J 3/128 |
| 2023/0136180 | A1 | 5/2023 | Abe | |
| 2025/0049645 | A1 * | 2/2025 | Kobayashi | A61Q 1/00 |

FOREIGN PATENT DOCUMENTS

| | | |
|---|---|---|
| EP | 3848412 | 7/2021 |
| JP | 2021138641 | 9/2021 |
| WO | 2009123148 | 10/2009 |
| WO | 2020188698 | 9/2020 |

OTHER PUBLICATIONS

Xingman Zhou; et al., "Effect of the degree of substitution on the hydrophobicity of acetylated cellulose for production of liquid marbles," Cellulose, vol. 23, No. 1, Jan. 6, 2016, pp. 811-821.

"Search Report of Europe Counterpart Application", issued on Feb. 27, 2024, p. 1-p. 6.

* cited by examiner

*Primary Examiner* — Jessica Worsham

(74) *Attorney, Agent, or Firm* — JCIPRNET

(57) ABSTRACT

Cellulose acetate particles include cellulose acetate as a main component, in which a total degree of acyl substitution of the cellulose acetate is 0.05 or more and less than 0.70.

12 Claims, No Drawings

CELLULOSE ACETATE PARTICLES

CROSS-REFERENCE TO RELATED APPLICATIONS

This application is based on and claims priority under 35 USC 119 from Japanese Patent Application No. 2023-052436 filed Mar. 28, 2023.

BACKGROUND

(i) Technical Field

The present disclosure relates to cellulose acetate particles.

(ii) Related Art

International Publication No. WO 2020/188698 proposes cellulose acetate-containing particles having an average particle diameter of 80 nm or more and 100 μm or less, a sphericity of 0.7 or more and 1.0 or less, a surface smoothness of 80% or more and 100% or less, and a surface contact angle to water of 100° or more, in which the total degree of acetyl substitution of the cellulose acetate is 0.7 or more and 2.9 or less.

International Publication No. WO 2009/123148 proposes cellulose derivative fine particles made of a cellulose derivative having some of cellulose hydroxy groups substituted with substituents, in which the average particle diameter is 9 to 1000 nm.

SUMMARY

Aspects of non-limiting embodiments of the present disclosure relate to cellulose acetate particles that remain soft and give less coarse feel even after long-term storage compared to cellulose acetate particles that contain cellulose acetate as a main component, in which a total degree of acyl substitution of the cellulose acetate is less than 0.05 or 0.70 or more.

Aspects of certain non-limiting embodiments of the present disclosure overcome the above disadvantages and/or other disadvantages not described above. However, aspects of the non-limiting embodiments are not required to overcome the disadvantages described above, and aspects of the non-limiting embodiments of the present disclosure may not overcome any of the disadvantages described above.

According to an aspect of the present disclosure, there is provided cellulose acetate particles including cellulose acetate as a main component, in which a total degree of acyl substitution of the cellulose acetate is 0.05 or more and less than 0.70.

DETAILED DESCRIPTION

One exemplary embodiment of the present disclosure will now be described. The following description and examples are merely exemplary embodiments and do not limit the scope of the disclosure.

In stepwise numerical ranges of the present description, the upper limit or the lower limit of one numerical range may be substituted with an upper limit or a lower limit of a different stepwise numerical range. In addition, in any numerical range described in this description, the upper limit or the lower limit of the numerical range may be substituted with a value indicated in Examples.

Each of the components may contain more than one corresponding substances.

When the amount of a component in a composition is described and when there are two or more substances that correspond to that component in the composition, the amount is the total amount of the two or more substances in the composition unless otherwise noted.

Cellulose Acetate Particles

The cellulose acetate particles of this exemplary embodiment contain a cellulose acetate as a main component, and the total degree of acyl substitution of cellulose acetate is 0.05 or more and less than 0.70.

The cellulose acetate particles of the present exemplary embodiment having the aforementioned features remain soft and rarely exhibit coarse feel even after long-term storage. The reason for this is presumably as follows.

Cellulose particles have a high elastic modulus and are hard. Thus, cellulose particles are unsuitable for the usage that involves softness. One example of the usage that involves softness is tactile sensation improver particles for cosmetic items.

In a known art for improving softness of cellulose particles, the tactile sensation has been improved by using cellulose acetate having a total degree of acetyl substitution controlled to be in the range of 0.7 to 2.9 (International Publication No. WO2020/188698 etc.).

However, according to this related art, introduction of acyl groups makes cellulose more prone to plasticization and solidification due to erosion of low-molecular-weight components (esters etc.). As a result, the long-term storage deteriorates the tactile sensation, and hardness and coarse feel are generated.

In contrast, according to this exemplary embodiment, cellulose acetate particles that contain cellulose acetate as a main component are applied. By setting the degree of acetyl substitution of cellulose acetate to 0.05 or more, the cellulose-derived strong molecular structure collapses, the tactile sensation is improved, the softness is maintained, and the coarse feel is rarely generated. Meanwhile, by setting the total degree of acyl substitution of cellulose acetate to less than 0.70, the erosion by low-molecular-weight components is reduced, the tactile sensation is maintained even after long-term storage, softness remains, and the coarse feel is reduced.

For the reason described above, it is presumed that the cellulose acetate particles of the present exemplary embodiment remain soft and rarely exhibit coarse feel even after long-term storage.

The cellulose acetate particles of the present exemplary embodiment will now be described in detail.

Cellulose Acetate

The cellulose acetate particles of this exemplary embodiment contain cellulose acetate as a main component.

The phrase “cellulose acetate particles contain cellulose acetate as a main component” means that the amount of cellulose acetate contained relative to the cellulose acetate particles is 90 mass % or more.

However, when the cellulose particles have a coating layer and an intermediate layer described below, the phrase “contain cellulose acetate as a main component” means that the amount of cellulose acetate contained relative to base particles is 90 mass % or more.

Cellulose acetate is a cellulose derivative in which at least some of cellulose hydroxy groups are substituted (acetylated) with acetyl groups.

Some of cellulose hydroxy groups of cellulose acetate may be substituted with acyl groups other than acetyl groups.

Here, the hydrocarbon group in the acyl groups other than acetyl groups may be linear, branched, or cyclic, is preferably linear or branched, and more preferably linear.

The hydrocarbon group in the acyl groups other than acetyl groups may be saturated or unsaturated but is preferably saturated.

The acyl group other than the acetyl group may be an acyl group having 2 or more and 6 or less carbon atoms.

The acyl groups other than acetyl groups may be acyl groups having a hydrogen atom substituted with a halogen atom (for example, a fluorine atom, a bromine atom, or an iodine atom), an oxygen atom, a nitrogen atom, or the like but are preferably unsubstituted acyl groups.

Examples of the acyl group other than the acetyl group include a propionyl group, a butyryl group (a butanoyl group), a propenoyl group, and a hexanoyl group. Among these, from the viewpoint of improving the biodegradation speed, the acyl group is preferably an acyl group having 2 or more and 4 or less carbon atoms and more preferably an acyl group having 2 or 3 carbon atoms.

Examples of cellulose acetate include cellulose monoacetate, cellulose diacetate (DAC), cellulose triacetate, cellulose acetate propionate (CAP), and cellulose acetate butyrate (CAB).

One cellulose acetate may be used alone or two or more cellulose acetates may be used in combination.

The total degree of acyl substitution of cellulose acetate is 0.05 or more and less than 0.70; however, from the viewpoints of improving the softness and reducing the coarse feel after the long-term storage, the total degree of acyl substitution is preferably 0.15 or more and 0.6 or less and more preferably 0.25 or more and 0.5 or less.

The acyl groups in cellulose acetate may be only acetyl groups. When the acyl groups in cellulose acetate are only acetyl groups, the cellulose-derived strong molecular structure collapses easily. Moreover, erosion by low-molecular-weight components is more easily reduced. Thus, even after long-term storage, the softness remains and the coarse feel is reduced.

The degree of substitution of cellulose acetate is an indicator of the extent to which hydroxy groups in cellulose are substituted with acyl groups. In other words, the degree of substitution is an indicator of the extent of acylation of cellulose acetate. Specifically, the degree of substitution means an intramolecular average of how many of the three hydroxy groups in a D-glucopyranose unit of cellulose acetate are substituted with acyl groups. The degree of substitution is determined from an infrared absorption spectrum (Spotlight 400, produced by PerkinElmer Inc.) through the intensity ratio between the cellulose-derived peak and the acyl group-derived peak.

The number-average molecular weight of cellulose acetate is preferably 37000 or more and more preferably 45000 or more.

The upper limit of the number-average molecular weight of cellulose acetate is not particularly limited and, for example, may be 100000 or less.

When the number-average molecular weight of cellulose acetate is 37000 or more, the biodegradability is enhanced, softness remains, and the coarse feel is reduced. The reason for this is presumably as follows.

When the number-average molecular weight is 37000 or more, the number of terminal hydroxy groups is inhibited from increasing, and the number of hydroxy groups per unit volume is reduced. Thus, the number of hydrogen bonds inside and outside the molecule and the bonding strength are inhibited from increasing, the hardness is reduced, and the softness is enhanced. As a result, the softness remains and the coarse feel is reduced.

The number-average molecular weight of cellulose acetate is measured by gel permeation chromatography (differential refractometer Optilab T-rEX produced by Wyatt Technology Corporation, multi angle light scattering detector DAWN HELEOS II produced by Wyatt Technology Corporation, column: TSKgel α-M and α-3000 one each produced by TOSOH CORPORATION) by using dimethylacetamide (0.1 M lithium chloride added) as a solvent.

Other Components

The cellulose acetate particles of this exemplary embodiment may contain other components. However, when the cellulose acetate particles contain the coating layer described below, these other components are contained in the base particles to be coated with the coating layer.

Examples of the other components include plasticizers, flame retardants, compatibilizers, release agents, light stabilizers, weather stabilizers, coloring agents, pigments, modifiers, anti-drip agents, antistatic agents, anti-hydrolysis agents, fillers, reinforcing agents (for example, glass fibers, carbon fibers, talc, clay, mica, glass flakes, milled glass, glass beads, crystalline silica, alumina, silicon nitride, aluminum nitride, and boron nitride), acid acceptors for preventing acetic acid release (oxides such as magnesium oxide and aluminum oxide, metal hydroxides such as calcium hydroxide, aluminum hydroxide, and hydrotalcite, calcium carbonate, and talc), and reactive trapping agents (for example, epoxy compounds, acid anhydride compounds, and carbodiimide).

The amount of the other components contained relative to the total amount of the cellulose acetate particles (or base particles) may be 0 mass % or more and 5 mass % or less for each component. Here. "0 mass %" means that other components are not contained.

Cellulose Acetate Particles Having Coating Layer

The cellulose acetate particles of this exemplary embodiment may include a base particle that contains cellulose acetate as a main component (hereinafter, may also be referred to as a cellulose acetate base particle) and a coating layer coating the base particle and containing at least one coating material selected from the group consisting of fatty acids, fatty acid metal salts, amino acid compounds, lipid compounds, silicone compounds, fluorine compounds, and ceramide compounds (hereinafter, such cellulose acetate particles may also be referred to as "coating-layer-containing cellulose acetate particles").

When the cellulose acetate particles of the present exemplary embodiment have the aforementioned feature, the cellulose acetate particles are likely to stay soft and the coarse feel is reduced even after long-term storage. Furthermore, deterioration of the biodegradability is also reduced. The reason for this is presumably as follows.

Fatty acids and fatty acid metal salts offer a sponge-like effect by forming a pseudo foam structure due to repulsion attributable to the repulsion force acting between the aliphatic groups, and the softness of the surfaces of the particles is enhanced. Thus, even after long-term storage, the softness remains and the coarse feel is reduced.

Furthermore, fatty acids and fatty acid metal salts themselves have strong water repellency and increase the hydrophobicity; thus, hydrolysis of the cellulose acetate is reduced, particle surface defects attributable to the initial biodegradation are avoided, and thus biodegradation can proceed evenly. Meanwhile, since these compounds are prone to local aggregation, gaps form in the surfaces and microorganisms can enter these gaps, thereby realizing excellent biodegradability.

Amino acid compounds have strong affinity and bondability to cellulose acetate and are easy to fix to the cellulose acetate particle surfaces. Furthermore, amino acid compounds themselves have a bending molecular structure, and further enhance the softness of cellulose acetate bonded thereto. Thus, even after a long-term storage, the softness remains and the coarse feel is reduced.

Furthermore, amino acid compounds have a strong tendency to form flat crystals after coating, and the increase in specific surface area can reduce contact between microorganisms and cellulose acetate in the initial stage and decreases the change in texture over time due to delayed biodegradation. Furthermore, since gaps form between the crystals, microorganisms can slowly enter the gaps, biodegradation proceeds evenly, and thus excellent biodegradability can be achieved.

Lipid compounds have strong bondability to cellulose acylate and are easy to fix to the cellulose acylate particle surfaces. Lipid compounds also decrease the friction coefficient of the particle surfaces. Thus, even after a long-term storage, the softness remains and the coarse feel is reduced.

Silicone compounds have strong bondability to cellulose acylate and are easy to fix to the cellulose acylate particle surfaces. Silicone compounds also decrease the friction coefficient of the particle surfaces. Thus, even after a long-term storage, the softness remains and the coarse feel is reduced.

Fluorine compounds have strong bondability to cellulose acylate and are easy to fix to the cellulose acylate particle surfaces. Fluorine compounds also decrease the friction coefficient of the particle surfaces. Thus, even after a long-term storage, the softness remains and the coarse feel is reduced.

Ceramide compounds have strong bondability to cellulose acylate and are easy to fix to the cellulose acylate particle surfaces. Ceramide compounds also decrease the friction coefficient of the particle surfaces. Thus, even after a long-term storage, the softness remains and the coarse feel is reduced.

Presumably thus, even after long-term storage, the softness remains and the coarse feel is reduced.

Base Particles

The base particles contain cellulose acetate as a main component.

Cellulose acetate contained in the base particles are the same as cellulose acetate described above, and preferable ranges thereof are also the same.

Coating Layer

The coating layer may contain at least one coating material selected from the group consisting of fatty acids, fatty acid metal salts, amino acid compounds, lipid compounds, silicone compounds, fluorine compounds, and ceramide compounds.

Fatty Acids

Fatty acids are linear or branched saturated or unsaturated fatty acids. Fatty acids may be mixtures of saturated fatty acids and unsaturated fatty acids.

From the viewpoint of improving the softness and reducing the coarse feel after long-term storage, the fatty acids may have 16 or more and 22 or less (preferably 18 or more and 20 or less) carbon atoms. Specific examples of the linear fatty acids having 16 or more and 22 or less carbon atoms include behenic acid, arachidic acid, and palmitic acid.

Fatty Acid Metal Salts

Fatty acid metal salts are linear or branched saturated or unsaturated fatty acid metal salts. From the viewpoint of improving the softness and reducing the coarse feel after long-term storage, fatty acid metal salts may be mixtures of saturated fatty acids and unsaturated fatty acids.

Examples of the fatty acid metal salts include metal salts of fatty acids having 16 or more and 22 or less (preferably 18 or more and 20 or less) carbon atoms. Examples of the metal salts of fatty acids having 16 or more and 22 or less carbon atoms include metal salts of stearic acid, metal salts of behenic acid, and metal salts of palmitic acid.

An example of the metal in the fatty metal salts is divalent metals.

Examples of the metal in linear fatty acid metal salts include magnesium, calcium, aluminum, barium, and zinc.

Here, when the fatty acids and fatty acid metal salts have 16 or more carbon atoms, the fatty acid group is short, and a sufficient sponge effect is obtained. Meanwhile, when the number of carbon atoms is 22 or less, repulsion of the fatty acid group is decreased, the affinity with cellulose acetate is sufficiently obtained, and thus delamination from the cellulose acetate particles rarely occurs. Thus, even after long-term storage, the softness remains and the coarse feel is reduced. Furthermore, sufficient biodegradability is also obtained.

Amino Acid Compounds

Amino acid compounds refer to amino acids and amino acid derivatives.

Examples of the amino acid compounds include lauryl leucine, lauryl arginine, and myristyl leucine.

Lipid Compounds

Representative examples of lipid compounds include phospholipids (lecithin and its hydrogenated products, phosphatidylic acid and/or its salts, phosphatidylinositol, phosphatidylethanolamine, phosphatidylglycerol, soybean-derived phospholipids, soybean-derived hydrogenated phospholipids, egg yolk-derived phospholipids, egg yolk-derived hydrogenated phospholipids, etc.).

Examples of the lipids include glycolipids (rice bran glycosphingolipids, glycosphingolipids, etc.) and complex lipids.

Silicone Compounds

Silicone compounds are compounds having siloxane chains.

Examples of the silicone compounds include dimethylpolysiloxane, methylphenylsiloxane, methylhydrogenpolysiloxane, decamethylpolysiloxane, dodecamethylpolysiloxane, tetramethyltetrahydrogenpolysiloxane, triethoxysilylethylpolydimethylsiloxyethyldimethicone, triethoxysilylethylpolydimethylsiloxyethylhexyldimethicone, acrylic-silicone graft polymers, organic silicone resin partially crosslinked organopolysiloxane polymers, tetramethyltetrahydrogencyclotetrasiloxane, trimethylsiloxysilicate, amino-modified silicone, carboxylic acid-modified silicone, fluorinated silicone, silicone gum, acrylic silicone, silicone resin, triethoxysilylethyl polydimethylsiloxyethyl dimethicone, and triethoxysilylethyl polydimethylsiloxyethylhexyl dimethicone.

Fluorine Compounds

Fluorine compounds are compounds having fluorine atoms.

Examples of the fluorine compounds include perfluoropolyether, perfluoroalkyl phosphate (mixtures of a diethanolamine salt of monoperfluoroalkylethyl phosphate and a diethanolamine salt of diperfluoroalkylethyl phosphate, fluoro(C9-15) alcohol phosphate, etc.), perfluoroalkylalkoxysilanes (perfluorooctyltriethoxysilane, perfluorocaprylyltriethoxysilylethyl methicone, etc.), fluorine-modified silicone, fluorine-modified polymers (a copolymer of diethylaminoethyl methacrylate/2-hydroxyethyl methacrylate/perfluorohexylethyl methacrylate, etc.), perfluoroalkylsilane, perfluoroalkyl group-containing ester, perfluoroalkyl phosphate, perfluoropolyether, fluorosilicone, fluorinated silicone resins, trimethoxy(3,3,3-trifluoropropyl)silane, and tridecafluorooctyltriethoxysilane.

Ceramide Compounds

Ceramides are compounds in which a sphingosine and a fatty acid are amide-bonded.

Examples of ceramides include natural ceramides, vegetable ceramides, human ceramides, and synthetic ceramides (pseudo-ceramides).

Examples of natural ceramides include ceramide 1, ceramide 2, ceramide 3, ceramide 4, ceramide 5, ceramide 6, and ceramide 7.

Examples of vegetable ceramides include ceramides extracted from rice bran, rice plant, corn, konnyaku, pineapple, etc.

Examples of human ceramide 1 (ceramide EOP), ceramide 2 (ceramide NG), ceramide 3 (ceramide NP), ceramide 4 (ceramide EOH), ceramide 5 (ceramide AG), ceramide 6II (ceramide AP), ceramide 7 (ceramide AH), ceramide 8, ceramide 9, and ceramide 10.

Examples of synthetic ceramides include hydroxypropylbispalmitamide MEA, hydroxypropylbislauramide MEA, and hydroxypropylbisisostearamide MEA.

From the viewpoints of improving the softness and reducing the coarse feel after the long-term storage, the coating amount of the coating layer relative to the base particle is preferably 0.1 mass % or more and 10 mass % or less, more preferably 0.5 mass % or more and 9 mass % or less, and yet more preferably 1 mass % or more and 8 mass % or less.

Here, the amount of the coating material contained relative to the entire coating layer is preferably 90 mass % or more and 100 mass % or less and more preferably 95 mass % or more and 100 mass % or less.

Intermediate Layer

The coating-layer-containing cellulose acetate particles may include an intermediate layer between the base particle and the coating layer. The intermediate layer may contain at least one intermediate material selected from the group consisting of polyamine compounds, polyquaterniums, polysaccharide compounds, and polyacrylic acids.

When the cellulose acetate particles of the present exemplary embodiment have the aforementioned feature, the cellulose acetate particles are likely to stay soft and the coarse feel is reduced even after long-term storage. Furthermore, the biodegradability is also improved. The reason for this is presumably as follows.

Polyamine compounds have high affinity to cellulose acetate and to a carboxylic acid moiety of a coating layer, such as a fatty acid or a fatty acid metal salt, and can selectively direct the aliphatic groups of the fatty acid or the fatty acid metal salt toward the surface of the coated particle, thereby further enhancing the effect of the coating layer. Thus, even after a long-term storage, the softness remains and the coarse feel is reduced. Furthermore, deterioration of the biodegradability is also reduced.

Polyquaterniums also have the same effect as the polyamine compound, and, even after long-term storage, the softness remains and the coarse feel is reduced. Furthermore, deterioration of the biodegradability is also reduced.

Polysaccharide compounds have a structure extremely similar to cellulose acetate, and the entire molecule covers more parts of cellulose acetate; however, a cushion state having gaps is created in some parts, and a coating layer, such as a fatty acid or a fatty acid metal salt, shows affinity on these parts. Thus, even after a long-term storage, the softness remains and the coarse feel is reduced. Furthermore, deterioration of the biodegradability is also reduced.

Polyacrylic acids, which have an appropriate degree of water absorbency, take in moisture in their molecules, and thus show affinity to the cellulose acetate surfaces already absorbing some water without decreasing the softness and show affinity to, for example, a fatty acid or a fatty acid metal salt due to its similar polarity, thereby enhancing the effect of the coating layer. Thus, even after a long-term storage, the softness remains and the coarse feel is reduced. Furthermore, deterioration of the biodegradability is also reduced.

Presumably thus, cellulose acetate particles that remain soft and exhibit less coarse feel after long-term storage can be obtained. Also presumably, deterioration of the biodegradability is reduced.

A polyamine compound is a generic name for aliphatic hydrocarbons having two primary amino groups.

Examples of the polyamine compound include polyalkyleneimine, polyallylamine, polyvinylamine, and polylysine.

From the viewpoint of improving the biodegradability, polyalkyleneimine preferably has a constitutional unit having an alkylene group having 1 or more and 6 or less carbon atoms (preferably 1 or more and 4 or less and more preferably 1 or more and 2 or less carbon atoms), and polyethyleneimine is more preferable.

Examples of the polyallylamine include homopolymers or copolymers of allylamine, allylamineamide sulfate, diallylamine, dimethylallylamine, etc.

Polyvinylamine is, for example, produced by hydrolysis of poly(N-vinylformamide) with an alkali, and a specific example thereof is “PVAM-0595B” produced by Mitsubishi Chemical Corporation.

Polylysine may be extracted from a natural product, produced by using transforming microorganisms, or synthesized chemically.

Examples of polyquaternium include polyquaternium-6, polyquaternium-7, polyquaternium-10, polyquaternium-11, polyquaternium-51, polyquaternium-61, and polyquaternium-64.

From the viewpoints of the softness and reducing the coarse feel after the long-term storage, the coating amount of the intermediate layer relative to the base particle is preferably 0.1 mass % or more and 20 mass % or less and more preferably 1 mass % or more and 10 mass % or less.

Here, the amount of the intermediate material contained relative to the entire intermediate layer is preferably 90 mass % or more and 100 mass % or less and more preferably 95 mass % or more and 100 mass % or less.

External Additive

Inorganic particles may be externally added to the cellulose acetate particles of this exemplary embodiment. External addition of inorganic particles reduces secondary aggregation of the particles, and the particles easily exhibit their inherent properties. Presumably thus, cellulose acetate particles that remain soft and exhibit less coarse feel even after long-term storage can be easily obtained. Also presumably, deterioration of the biodegradability is reduced.

The external additive may be at least one selected from the group consisting of silicon-containing compound particles and metal oxide particles.

Silicon-containing compound particles refer to particles that contain silicon.

Silicon-containing compound particles may be particles solely composed of silicon or may be particles that contain silicon and other elements.

The silicon-containing compound particles may be silica particles. Silica particles may be any particles containing silica, that is, $SiO_2$, as a main component and may be crystalline or amorphous. The silica particles may be produced by using a silicon compound, such as water glass or alkoxysilane, as a raw material, and may be obtained by crushing quartz.

Oxides of metals other than silicon can be used as the metal oxide.

Examples of the metal oxide include zinc oxide, magnesium oxide, iron oxide, and aluminum oxide.

From the viewpoint of the texture (specifically, touch to the skin), the volume-average particle diameter of the external additive is preferably 1 nm or more and 100 nm or less and more preferably 5 nm or more and 30 nm or less.

The volume-average particle diameter of the external additive is measured by the same method as measuring the volume-average particle diameter of the cellulose acetate particles.

The amount of the external additive externally added relative to the entire mass of cellulose acetate particles (cellulose acetate particles without external addition of the external additive) may be 0.1 mass % or more and 5 mass % or less.

Volume-Average Particle Diameter and Large-Diameter-Side Number-Average Particle Size Distribution Index GSDv The volume-average particle diameter of the cellulose acetate particles according to the present exemplary embodiment is preferably more than 1 μm and 100 μm or less and more preferably 3 μm or more and 80 μm or less.

When the volume-average particle diameter of the cellulose acetate particles of the present exemplary embodiment is more than 1 μm and 100 μm or less, the cellulose acetate particles are likely to stay soft and the coarse feel is reduced even after long-term storage. Furthermore, deterioration of the biodegradability is also reduced. The reason for this is presumably as follows.

As long as the volume-average particle diameter is more than 1 μm, the hard portion at the center core of each particle has little influence, and thus the softness tends to be excellent. Thus, even after a long-term storage, the softness remains and the coarse feel is reduced.

When the volume-average particle diameter is 100 μm or less, the softness can be exhibited as the top surface absorbs water, and thus the softness tends to be excellent. Thus, even after a long-term storage, the softness remains and the coarse feel is reduced.

Moreover, since the surface area increases appropriately, the biodegradation occurring from the surface easily proceeds evenly, and the biodegradability tends to be excellent.

The volume-average particle diameter of the cellulose acetate particles is measured by the following procedure.

Particle diameters are measured with an LS particle size distribution meter "Beckman Coulter LS13320 (produced by Beckman Coulter Inc.)", the particle diameter accumulation distribution is plotted from the small-diameter-side on a volume basis, and the particle diameter at 50% accumulation is determined as the volume-average particle diameter.

Method for Producing Cellulose Acetate Particles

A method for producing cellulose acetate particles according to an exemplary embodiment is, for example, as follows.

Step of Producing Cellulose Acetate Particles (Base Particles)

(1) First, cellulose acetate is dissolved in a water-soluble organic solvent A to prepare a cellulose acylate solution A.

(2) Next, the cellulose acylate solution A is added to a calcium carbonate dispersion containing calcium carbonate dispersed in water, followed by stirring, to prepare a cellulose acylate solution B.

(3) Next, the cellulose acylate solution B is added to a mixed solution of carboxymethyl cellulose, a water-soluble organic solvent B, and water, followed by high speed stirring, to prepare a cellulose acylate solution C.

(4) Next, sodium hydroxide is added to the cellulose acylate solution C, a cellulose acylate dispersion C is heated to remove the water-soluble organic solvents A and B, and hydrochloric acid is added to the resulting mixture to form cellulose acylate particles. Then the cellulose acylate particles are filtered out and dispersed in water to prepare a cellulose acylate particle dispersion.

(5) Next, sodium hydroxide is added to the cellulose acylate particle dispersion, and then the resulting cellulose acylate particle dispersion is heated in a weakly alkaline environment and stirred to saponify the cellulose acylate particles.

(6) Next, hydrochloric acid is added to a cellulose acylate particle suspension having the adjusted substitution degree to set the pH of the suspension to near neutral (for example, in the range of 6.5 or more and 7 or less), and then filtration and washing with pure ware are repeated on the cellulose acetate particles. After the electrical conductivity of the filtrate has reached 10 μs/cm or less, the filtered out cellulose acylate particles are dried.

Cellulose acetate particles having the aforementioned degree of substitution are obtained by performing (A) adjustment of the saponification temperature and saponification time and (B) a process of raising the alkali permeability of the cellulose acylate particles during saponification (for example, a process of adding a water-soluble organic solvent D to the dispersion after preparing the cellulose acylate particle dispersion before saponification) in the production process described above.

Here, the water-soluble organic solvent A is a solvent in which 0.1 mass % or more and 10 mass % of water dissolves at 25° C. relative to the solvent, and examples thereof include ethyl acetate and butyl acetate.

The water-soluble organic solvent B is a solvent in which 0.1 mass % or more and 10 mass % of water dissolves at 25° C. relative to the solvent, and examples thereof include methyl ethyl ketone and acetone.

The water-soluble organic solvent D is a solvent in which 0.1 mass % or more and 10 mass % of water dissolves at 25° C. relative to the solvent, and examples thereof include ethyl acetate, butyl acetate, methyl ethyl ketone, and acetone.

The cellulose acylate particles (base particles) that have the degree of acetyl substitution specified above according to the present exemplary embodiment may be produced by any method other than the one described above, and, for example, may be obtained by the following methods by using cellulose acylate that already has the degree of acetyl substitution specified above.

1) A kneading and crushing method that involves kneading raw materials and crushing and classifying the resulting kneaded product to obtain particles.
2) A dry method that involves changing the shape of the particles obtained by the kneading and crushing method with mechanical impact or thermal energy so as to obtain particles.
3) An aggregation and coalescence method that involves mixing dispersions of raw material particles and aggregating and thermally fusing the particles in the resulting dispersion so as to obtain particles.
4) A dissolution and suspension method that involves suspending, in an aqueous medium, an organic solvent in which raw materials are dissolved so as to form particles containing the respective components.

Step of Forming Intermediate Layer and Coating Layer

When producing coating-layer-containing cellulose acetate particles, a step (coating layer forming step) of forming a coating layer may be performed after the aforementioned cellulose acetate particle (base particle) production process.

When the coating layer forming step is to be performed, a coating layer is formed by using, as base particles, particles obtained by the cellulose acetate particle (base particle) production process described above.

First, a water dispersion in which base particles are dispersed is prepared. Prior to preparing the water dispersion, the base particles may be washed with an acid.

Next, the water dispersion containing the dispersed base particles is mixed with an aqueous solution containing an intermediate material constituting the intermediate layer. As a result, for example, the hydroxy groups in cellulose acetate contained in the base particles and the functional groups (amine sites, carboxyl groups, amino groups, etc.) of the intermediate material constituting the intermediate layer react with each other, and the hydroxy groups hydrogen-bond with each other to form an intermediate layer. Next, the water dispersion containing the base particles having the intermediate layer is mixed with an emulsion containing a coating material that constitutes a coating layer. As a result, a coating layer is formed.

When the intermediate layer is not formed, a coating layer is formed by mixing a water dispersion in which the base particles obtained by the aforementioned cellulose acetate particle (base particle) production process are dispersed, and an emulsion containing a compound constituting the coating layer.

Then coating-layer-containing cellulose acetate particles are taken out from the mixture. The coating-layer-containing cellulose acetate particles are taken out by filtering the mixture, for example. The coating-layer-containing cellulose acetate particles that have been taken out may be washed with water. As a result, the unreacted surface-treating polymers can be removed. Next, the coating-layer-containing cellulose acetate particles are dried to obtain cellulose acetate particles of the present exemplary embodiment.

External Addition Step

An external additive may be added to the obtained cellulose acetate particles.

In the external addition step, for example, an external additive is added to the cellulose acetate particles by using a mixing mill, a V blender, a Henschel mixer, a Lodige mixer, or the like.

Usage

Examples of the usage of the cellulose acetate particles of the present exemplary embodiment include particles for cosmetics, rolling agents, abrasives, scrubbing agents, display spacers, bead molding materials, light diffusing particles, resin reinforcing agents, refractive index controllers, biodegradation accelerators, fertilizers, water-absorbing particles, toner particles, and anti-blocking particles.

A preferable usage of the cellulose acetate particles of the present exemplary embodiment is cosmetics.

In particular, the cellulose acetate particles of the present exemplary embodiment are preferably used as cosmetic additives.

Since the cellulose acetate particles of the present exemplary embodiment have excellent softness, a cosmetic item containing the cellulose acetate particles as a cosmetic additive spreads smoothly with less friction over the skin when the cosmetic item is applied to the skin.

The cellulose acetate particles of the present exemplary embodiment can be applied to cosmetic additives such as cosmetic items for base makeup (for example, makeup bases, concealers, foundations, and face powders), cosmetic items for makeups (for example, lipsticks, lip-glosses, lipliners, blushes, eyeshadows, eyeliners, mascaras, eyebrow pencils, nail manicures, and nail caring cosmetic items), and cosmetic items for skin care (for example, face wash formulations, face cleansers, lotions, milky lotions, serums, packs, facial masks, and cosmetic items for caring areas around eyes and mouth).

In particular, since the cosmetic additives for makeup cosmetic items favor softness and biodegradability, the resin particles of the present exemplary embodiment may be used as the cosmetic additives for makeup cosmetic items.

EXAMPLES

Examples, which do not limit the scope of the present disclosure, will now be described. In the description below, "parts" and "%" are all on a mass basis unless otherwise noted.

Preparation of Individual Materials

The following materials are prepared.

Cellulose Acylate

CA-1: diacetyl cellulose, "L50" produced by Daicel Corporation, number-average molecular weight: 58000

CA-2: diacetyl cellulose, "L20" produced by Daicel Corporation, number-average molecular weight: 47000

CA-3: cellulose acetate propionate, "CAP482-0.5" produced by Eastman Chemical Company, number-average molecular weight: 25000

Coating Material

ST-1: calcium stearate (fatty acid metal salt), "CALCIUM STEARATE SHOKUBUTSU" produced by NOF CORPORATION ST-2: behenic acid (fatty acid), "NAA-222S" produced by NOF CORPORATION ST-3: Lauroyl lysine (amino acid compound) "AMIHOPE LL" produced by AJINOMOTO CO., INC.

ST-4: hydrogenated lecithin (lipid compound) "NIKKOL Lecinol S-10" produced by Nikko Chemicals Co., Ltd.

ST-5: hydrogen dimethicone (silicone compound) "KF-9901" produced by Shin-Etsu Chemical Co., Ltd.

ST-6: perfluorooctyltriethoxysilane (fluorine compound "Perfluorooctyl Triethoxysilane" produced by Fuluorochem ST-7: Hydroxypropyl bispalmitamide MEA (ceramide compound), "PACIFICOS CRM" produced by MACROCARE Tech. Co., Ltd.

ST-8: polyvinylpyrrolidone, "PVP" produced by NIPPON SHOKUBAI CO., LTD.

Intermediate Material

AA-1: polyethyleneimine (polyamine compound), "PEI-1500" produced by NIPPON SHOKUBAI CO., LTD.

AA-2: polyquaternium 11 (polyquaternium), "LUVIQUAT PQ11AT1" produced by BASF Japan AA-3: cationated guar gum (polysaccharide), "RHABALL GUM CG-M" produced by Sumitomo Pharma Food & Chemical Co., Ltd.

AA-4: polyacrylic acid, "JURYMER AC-10H" produced by TOAGOSEI CO., LTD.

AA-5: carbomer, "NTC-CARBOMAER 380" produced by Nikko Chemicals Co., Ltd.

EA-1: dimethysilicated silica, "AEROSIL R972" produced by Nippon Aerosil Co., Ltd., volume-average particle diameter: 16 nm EA-2: silica dimethicone silylate, "AEROSIL RY200S" produced by Nippon Aerosil Co., Ltd., volume-average particle diameter: 16 nm

Examples 1 to 22 and Comparative Examples 1 to 4

Formation of Base Particles

In 870 g of ethyl acetate, 130 g of cellulose acylate of the type indicated in Table 1 is dissolved. The resulting solution is added to a dispersion prepared by dispersing 50 g of calcium carbonate in 500 g of pure water, and the resulting mixture is stirred for 3 hours. The resulting mixture is added to a dispersion prepared by dispersing 4 g of carboxymethyl cellulose and 200 g of methyl ethyl ketone in 600 g of pure water, and the resulting mixture is stirred for 5 hours in a high-speed emulsifier machine. Thereto, 10 g of sodium hydroxide is added, followed by stirring at 80° C. for 3 hours to remove ethyl acetate and methyl ethyl ketone. Thereto, 10 g of diluted hydrochloric acid is added to dissolve calcium carbonate. The residue is filtered and is again dispersed in pure water to obtain a base particle slurry. To the base particle slurry before saponification, 10 g of ethyl acetate or 30 g of methyl ethyl ketone (MEK) serving as a solvent is added according to Table 1.

Saponification of Base Particles

To 500 parts by mass of the base particle slurry (solid content: 10%), 17.5 parts by mass of 20% NaOH is added and the resulting mixture is stirred at a saponification temperature for a saponification time indicated in Table 1 so as to saponify the base particles. Hydrochloric acid is added to the saponified base particle slurry to adjust the pH to 7. Next, filtration and washing are repeated until the filtrate is washed until the electrical conductivity of the filtrate is 10 μs/cm or less. The obtained base particles are dried at 80° C. for 3 hours to remove the solvent. As a result, a base particle cake is obtained.

Surface Treatment

The washed base particle cake is reslurried with ion exchange water to adjust to 500 g. the intermediate material of a type and in a coating amount indicated in Table 1 is added thereto, followed by stirring for 1 hour, and then the intermediate material of a type and in a coating amount indicated in Table 1 is added thereto, followed by stirring for 24 hours. As a result, an intermediate layer and a coating layer are formed on a base particle.

Next, the base particles having an intermediate layer and a coating layer formed thereon are repeatedly filtered and washed until the filtrate exhibits an electrical conductivity of 10 μs/cm or less. After washing, the obtained cake is dried to obtain cellulose acetate particles having an intermediate layer and a coating layer.

The obtained particles are stirred in an FM mixer (FM40 produced by NIPPON COKE & ENGINEERING. CO., LTD.) by maintaining the mixer temperature at 25° C. at a rotation rate of 2000 min-1 for 3 hours to dress the surface of the coating layer.

External Addition Treatment

Next, to 100 parts of cellulose acetate particles having the intermediate layer and the coating layer, the external additive of a type and in an amount (parts) indicated in Table 1 is added, and the resulting mixture is mixed in a mixing mill (WONDER CRUSHER produced by OSAKA CHEMICAL Co., Ltd.) to obtain cellulose acetate particles having an external additive.

Here, as indicated by "-" in Table 1, in some examples, cellulose acetate particles are produced by omitting at least one selected from formation of an intermediate layer, formation of a coating layer, and addition of an external additive.

Furthermore, in some examples, cellulose acetate particles are produced without adding 10 g of ethyl acetate or 30 g of methyl ethyl ketone (MEK) serving as a solvent to the base particle slurry before saponification.

Furthermore, in some examples, cellulose acetate particles are produced without saponification of the base particles.

TABLE 1

| | Particle No. | Raw material cellulose acetate | Solvent added before saponification | 20% NaOH/parts by mass | Saponification temperature/° C. | Saponification time/h | Degree of acetyl substitution | Degree of propionyl substitution | Total degree of acyl substitution | Surface treatment: Coating layer (coating material type/coating amount % (relative to base particles)) | Surface treatment: Intermediate layer (intermediate material type/coating amount % (relative to base particles)) | Surface treatment: External additive (type/parts) | Particle diameter/μm |
|---|---|---|---|---|---|---|---|---|---|---|---|---|---|
| | | Cellulose acetate particles (base particles) | | | | | | | | | | | |
| Example 1 | PTC-1 | CA-1 | Ethyl acetate | 17.5 | 15 | 9 | 0.5 | 0 | 0.5 | ST-1/8% | AA-1/1% | EA-1/1% | 7 |
| Example 2 | PTC-2 | CA-1 | Ethyl acetate | 17.5 | 15 | 24 | 0.05 | 0 | 0.05 | ST-1/8% | AA-1/1% | EA-1/1% | 7 |
| Example 3 | PTC-3 | CA-1 | Ethyl acetate | 17.5 | 15 | 6 | 0.68 | 0 | 0.68 | ST-1/8% | AA-1/1% | EA-1/1% | 7 |
| Example 4 | PTC-4 | CA-1 | Ethyl acetate | 17.5 | 15 | 9 | 0.5 | 0 | 0.5 | — | — | — | 5 |
| Example 5 | PTC-5 | CA-1 | Ethyl acetate | 17.5 | 15 | 24 | 0.05 | 0 | 0.05 | — | — | — | 5 |
| Example 6 | PTC-6 | CA-1 | Ethyl acetate | 17.5 | 15 | 15 | 0.16 | 0 | 0.16 | — | — | — | 7 |
| Example 7 | PTC-7 | CA-1 | Ethyl acetate | 17.5 | 15 | 12 | 0.3 | 0 | 0.3 | — | — | — | 7 |
| Example 8 | PTC-8 | CA-1 | Ethyl acetate | 17.5 | 15 | 15 | 0.6 | 0 | 0.6 | — | — | — | 7 |
| Example 9 | PTC-9 | CA-1 | Ethyl acetate | 17.5 | 15 | 6 | 0.68 | 0 | 0.68 | — | — | — | 5 |
| Example 10 | PTC-10 | CA-1 | Ethyl acetate | 17.5 | 15 | 9 | 0.5 | 0 | 0.5 | — | — | — | 95 |
| Example 11 | PTC-11 | CA-2 | MEK | 17.5 | 15 | 9 | 0.5 | 0 | 0.5 | ST-1/7% | AA-2/1% | — | 10 |
| Example 12 | PTC-12 | CA-2 | MEK | 17.5 | 15 | 9 | 0.5 | 0 | 0.5 | ST-1/7% | AA-3/1% | — | 10 |
| Example 13 | PTC-13 | CA-2 | MEK | 17.5 | 15 | 9 | 0.5 | 0 | 0.5 | ST-1/7% | AA-4/1% | — | 10 |
| Example 14 | PTC-14 | CA-1 | MEK | 17.5 | 15 | 9 | 0.5 | 0 | 0.5 | ST-2/8% | AA-1/2% | — | 10 |
| Example 15 | PTC-15 | CA-1 | MEK | 17.5 | 15 | 9 | 0.5 | 0 | 0.5 | ST-3/8% | AA-1/2% | — | 10 |
| Example 16 | PTC-16 | CA-1 | MEK | 17.5 | 15 | 9 | 0.5 | 0 | 0.5 | ST-4/8% | AA-4/1% | — | 7 |
| Example 17 | PTC-17 | CA-1 | MEK | 17.5 | 15 | 9 | 0.5 | 0 | 0.5 | ST-5/8% | AA-4/1% | — | 7 |
| Example 18 | PTC-18 | CA-1 | MEK | 17.5 | 15 | 9 | 0.5 | 0 | 0.5 | ST-6/8% | AA-4/1% | — | 7 |
| Example 19 | PTC-19 | CA-1 | MEK | 17.5 | 15 | 9 | 0.5 | 0 | 0.5 | ST-7/8% | AA-4/1% | — | 7 |
| Example 20 | PTC-20 | CA-1 | MEK | 17.5 | 15 | 9 | 0.5 | 0 | 0.5 | ST-1/10% | AA-1/5% | EA-2/1% | 7 |
| Example 21 | PTC-21 | CA-1 | MEK | 17.5 | 15 | 9 | 0.5 | 0 | 0.5 | ST-8/8% | AA-5/1% | — | 7 |
| Example 22 | PTC-22 | CA-3 | MEK | 17.5 | 15 | 9 | 0.1 | 0.4 | 0.5 | — | — | — | 7 |
| Comparative Example 1 | PTC-23 | CA-1 | — | — | 30 | 6 | 0 | 0 | 0 | — | — | — | 7 |
| Comparative Example 2 | PTC-24 | CA-1 | — | — | 30 | 6 | 0 | 0 | 0 | ST-1/8% | AA-1/1% | EA-1/1% | 7 |
| Comparative Example 3 | PTC-25 | CA-1 | — | Saponification of base particles omitted | | | 2.4 | 0 | 2.4 | — | — | — | 6 |
| Comparative Example 4 | PTC-26 | CA-3 | — | | | | 0.2 | 2.5 | 2.7 | — | — | — | 6 |

Evaluation of Physical Properties

Properties of Particles

For cellulose acetate particles of each of the examples, the following properties of the particles were measured according to the methods described above.

The degree of acetyl substitution of cellulose acetate

The degree in which cellulose acetate is substituted by substituents other than acetyl groups Volume-average particle diameter (in the table, also indicated as "Particle diameter")

Evaluation of Cosmetic Items

Preparation of Cosmetic Items

Among the cellulose particles of Examples, the cellulose particles indicated in Table 3 are used to prepare various types of cosmetic items. Specific details are as follows.

Liquid Foundation

A liquid foundation is obtained by a known method according to the formulation indicated in Table 2-1.

TABLE 2-1

| Liquid foundation | | | |
|---|---|---|---|
| Formulation | Compound | Product name (manufacturer) | Parts by mass |
| Particles | Particles | Cellulose acetate particles indicated in Table 3 | 10 |
| Formulation other than particles | Propylene glycol | Propylene Glycol JSQI (Dow Toray Co., Ltd.) | 5 |
| | Bentonite | OVWIL BR (MIZUSAWA INDUSTRIAL CHEMICALS, LTD.) | 1 |
| | Triethanolamine | Triethanolamine 99%(Dow Toray Co., Ltd.) | 1 |
| | Stearic acid | NAA172 (NOF CORPORATION) | 3 |
| | Stearyl alcohol | NAA45 (NOF CORPORATION) | 1 |
| | Liquid paraffin | MORESCO VIOLESS (MORESCO) | 8 |
| | Isopropyl myristate | IPM-R (NOF CORPORATION) | 5 |
| | Vaseline | NOMCORT W (The Nisshin OilliO Group, Ltd.) | 2 |
| | Monoglyceride stearate | EXCEL84 (Kao Corporation) | 2 |
| | POE(20) stearyl ether | EMALEX602 (NIHON EMULSION Co., Ltd.) | 1 |
| | Titanium oxide | MKR-1 (SAKAI CHEMICAL INDUSTRY CO., LTD.) | 8 |
| | Kaolin | BERACLAY 20061 AMAZONIAN WHITE CLAY (BERECA) | 5 |
| | Iron oxide | C33-128 Sun CROMA RED Iron Oxide (Sun Chemical) | 0.5 |
| | Preservative | POTIPHEN HD (Ashland Japan) | 0.5 |
| | Fragrance | Bisabolol rac. (BASF Japan) | 0.3 |
| | Purified water | | 46.5 |
| | | Total | 100 |

Milky Lotion

A milky lotion is obtained by a known method according to the formulation indicated in Table 2-2.

TABLE 2-2

| Milky lotion | | | |
|---|---|---|---|
| Formulation | Compound | Product name (manufacturer) | Parts by mass |
| Particles | Particles | Cellulose acetate particles indicated in Table 3 | 2 |
| Formulation other than particles | Propylene glycol | Propylene Glycol JSQI (Dow Toray Co., Ltd.) | 5 |
| | Polyethylene glycol 1500 | PEG#1500 (NOF CORPORATION) | 3 |
| | Carboxyvinyl polymer | NTC-CARBOMER 380 (Nikko Chemicals Co., Ltd.) | 0.1 |
| | Triethanolamine | Triethanolamine 99% (Dow Toray Co., Ltd.) | 1 |
| | Stearic acid | NAA172 (NOF CORPORATION) | 2 |
| | Setanol | NAA44 (NOF CORPORATION) | 1.5 |
| | Liquid paraffin | MORESCO VIOLESS (MORESCO) | 10 |
| | Vaseline | NOMCORT W (The Nisshin OilliO Group, Ltd.) | 3 |
| | Glyceryl oleate | NIKKOL MGO (Nikko Chemicals Co., Ltd.) | 1 |
| | POE(20) sorbitan oleate | NIKKOL TO −0 V (Nikko Chemicals Co., Ltd.) | 1 |
| | Preservative | POTIPHEN HD (Ashland Japan) | 0.2 |
| | Fragrance | Bisabolol rac. (BASF Japan) | 0.1 |
| | Purified water | | 70.1 |
| | | Total | 100 |

Loose Powder

The formulation indicated in Table 2-3 is mixed with a blender, crushed with a crusher, and sifted through a 250 μm screen to obtain a loose powder.

TABLE 2-3

Loose powder

| Formulation | Compound | Product name (manufacturer) | Parts by mass |
|---|---|---|---|
| Particles | Particles | Cellulose acetate particles indicated in Table 3 | 10 |
| Formulation other than particles | Talc | Talc CT-25 (YAMAGUCHI MICA CO., LTD.) | 65 |
| | Kaolin | BERACLAY 20061 AMAZONIAN WHITE CLAY (BERECA) | 5 |
| | Titanium oxide | MKR-1 (SAKAI CHEMICAL INDUSTRY CO., LTD.) | 3 |
| | Zinc myristate | POWDER BASE M (NOF CORPORATION) | 5 |
| | Magnesium carbonate | Narrasorb HFB (Nouryon Japan) | 5 |
| | Sericite | Sericite FSE (SANSHIN MINING IND. CO., LTD.) | 7 |
| | | Total | 100 |

Powder Foundation

According to the formulation indicated in Table 2-4, particles and powders are mixed, binders are separately mixed, a mixture of the particles and the powders is gradually added to the binders under stirring, and the resulting mixture is mixed to obtain a powder foundation.

TABLE 2-4

Powder foundation

| Formulation | Compound | Product name (manufacturer) | Parts by mass |
|---|---|---|---|
| Particles | Particles | Cellulose acetate particles indicated in Table 3 | 8 |
| Powders other than particles mentioned above | Talc | Talc CT-25 (YAMAGUCHI MICA CO., LTD.) | 52.5 |
| | Mica | Mica FA450 (YAMAGUCHI MICA CO., LTD.) | 16 |
| | Titanium oxide | MKR-1 (SAKAI CHEMICAL INDUSTRY CO., LTD.) | 12 |
| | Black iron oxide | C33-134 Sun CROMA Black Iron Oxide (Sun Chemical) | 0.2 |
| | Red iron oxide | C33-128 Sun CROMA Red Iron Oxide (Sun Chemical) | 0.4 |
| | Yellow iron oxide | C33-210 Sun CROMA Yellow Iron Oxide (Sun Chemical) | 2.4 |
| Binder | Diisostearyl malate | Neosolue-DiSM (NIPPON FINE CHEMICAL CO., LTD) | 3 |
| | Caprylic/capric triglyceride | Caprylic/Capric Triglyceride (FUJIFILM Wako Pure Chemical Corporation) | 2 |
| | Neopentyl glycol dicaprate | NPDC (KOKYU ALCOHOL KOGYO CO., LTD.) | 2 |
| | Pentylene glycol | DIOL PD (KOKYU ALCOHOL KOGYO CO., LTD.) | 1.5 |
| | | Total | 100 |

Sunscreen Cream

According to the formulation indicated in Table 2-5, an oil phase (1) is melted by heating at 50° C., and an oil phase (2) is added thereto, followed by mixing. Meanwhile, a water phase (2) is dissolved and mixed. To the mixture of the oil phases (1) and (2), particles and powders are added, followed by dispersing and mixing, then the mixture of the water phases (1) and (2) is gradually added thereto, and the resulting mixture is emulsified to obtain a sunscreen cream.

TABLE 2-5

Sunscreen cream

| Formulation | Compound | Product name (manufacturer) | Parts by mass |
|---|---|---|---|
| Particles | Particles | Cellulose acetate particles indicated in Table 3 | 5 |
| Powders | Quaternium-18 Hectorite | SUMECTON SAN (KUNIMINE | 1 |

TABLE 2-5-continued

| Sunscreen cream | | | |
|---|---|---|---|
| Formulation | Compound | Product name (manufacturer) | Parts by mass |
| other than particles mentioned above | | INDUSTRIES CO., LTD.) | |
| | Titanium oxide | MKR-1 (SAKAI CHEMICAL INDUSTRY CO., LTD.) | 8 |
| Oil phase (1) | Ethylhexyl methoxycinnamate | Uvinul MC80 (BASF Japan) | 4 |
| | t-Butylmethoxydibenzoyl methane | Eusolex 9030 (Merk KGaA) | 0.5 |
| | Bisethylhexyloxyphenol methoxyphenyltriazine | Tinosorb S (BASF Japan) | 2 |
| | Isopropyl sebacate | Isopropyl sebacate (FUJIFILM Wako Pure Chemical Corporation) | 6 |
| | Caprylic/capric triglyceride | Caprylic/Capric Triglyceride (FUJIFILM Wako Pure Chemical Corporation) | 2 |
| Oil phase (2) | Cetyl PEG/PPG-10/1 dimethicone | KF-6048 (Shin-Etsu Chemical Co., Ltd.) | 4 |
| | Sorbitan isostearate | EMALEX SPIS100 (NIHON EMULSION Co., Ltd.) | 0.4 |
| | Cyclopentanesiloxane | KF-995 (Shin-Etsu Chemical Co., Ltd.) | 16 |
| | Ethylhexylglycerin glyceryl caprylate | NIKKOL Nikkoguard 88 (Nikko Chemicals Co., Ltd.) | 0.4 |
| Water phase (1) | (PEG-240/decyltetradeceth-20/HDI) copolymer | ADEKA NOL GT-700 | 1 |
| | Glycerin | RG•CO•P (NOF CORPORATION) | 4 |
| | 1,3-Butylene glycol | HAISUGARCANE BG (KOKYU ALCOHOL KOGYO CO., LTD.) | 4 |
| | Pentylene glycol | DIOL PD (KOKYU ALCOHOL KOGYO CO., LTD.) | 1 |
| | Phenoxy ethanol | Phenoxetol (Clariant Japan) | 0.3 |
| Water phase (2) | Magnesium sulfate | Magnesium sulfate (FUJIFILM Wako Pure Chemical Corporation) | 0.3 |
| | Purified water | | 40.1 |
| | | Total | 100 |

All-In-One Gel

According to the formulation indicated in Table 2-6, a water phase (1) and a water phase (2) are mixed. Next, an oil phase (1) is mixed and added to the mixture of the water phases (1) and (2). After an oil phase (2) is heated to 70° C., and particles are added thereto to obtain a dispersion. The obtained dispersion is added to the mixture of the water phases (1) and (2) and the oil phase (1), and the resulting mixture is stirred and emulsified by mixing. A neutralizer is added thereto, and the resulting mixture is stirred and cooled to obtain an all-in-one gel.

TABLE 2-6

| All-in-one gel | | | |
|---|---|---|---|
| Formulation | Compound | Product name (manufacturer) | Parts by mass |
| Particles | Particles | Cellulose acetate particles indicated in Table 3 | 4 |
| Oil phase (1) | Xanthan gum | NOMCORT Z (The Nisshin OilliO Group, Ltd.) | 0.1 |
| | Hydrogenated lecithin | COATSOME NC-21 (NOF CORPORATION) | 0.1 |
| | Glycerin | RG•CO•P (NOF CORPORATION) | 5 |
| | Isopentyldiol | Isoprene glycol (KURARAY CO., LTD.) | 4 |
| Oil phase (2) | Polyglyceryl-10 stearate | SUNSOFT Q-18S-C (Taiyo Kagaku Co., Ltd.) | 1.2 |
| | Polyglyceryl-4 stearate | NIKKOL Tetraglyn 1-SV (Nikko Chemicals Co., Ltd.) | 0.3 |
| | Behenyl alcohol | NAA-422 (NOF CORPORATION) | 1.8 |
| | Octyldodecanol | RISONOL 20SP (KOKYU ALCOHOL KOGYO CO., LTD.) | 0.8 |
| | Cetyl ethylhexanoate | FineNeo-CIO (NIPPON FINE CHEMICAL CO., LTD) | 3.2 |
| | Squalane | NIKKOL Purified Olive Squalane (Nikko Chemicals Co., Ltd.) | 0.6 |
| | Tocopherol | Tocopherol 100 (The Nisshin OilliO Group, Ltd.) | 0.6 |

TABLE 2-6-continued

| All-in-one gel | | | |
|---|---|---|---|
| Formulation | Compound | Product name (manufacturer) | Parts by mass |
| | Ethylhexylglycerin glyceryl caprylate | NIKKOL Nikkoguard 88 (Nikko Chemicals Co., Ltd.) | 0.6 |
| Water phase (1) | Carboxyvinyl polymer | NTC-CARBOMER 380 (Nikko Chemicals Co., Ltd.) | 0.4 |
| | Pentylene glycol | DIOL PD (KOKYU ALCOHOL KOGYO CO., LTD.) | 1 |
| | Phenoxy ethanol | Phenoxetol (Clariant Japan) | 0.3 |
| | Sodium dilauramidoglutamide lysine, water | Pellicer LB100 (ASAHI KASEI FINECHEM CO., LTD) | 0.1 |
| Water phase (2) | Citric acid | Citric acid (FUJIFILM Wako Pure Chemical Corporation) | 0.1 |
| | Purified water | | 1.4 |
| | Neutralizer: 10% aqueous sodium hydroxide solution | | |
| | | Total | 100 |

Makeup Base

According to the formulation indicated in Table 2-7, particles are dispersed in a component A, followed by stirring. A component B is added thereto, and the resulting mixture is stirred to obtain a makeup base.

TABLE 2-7

| Makeup base | | | |
|---|---|---|---|
| Formulation | Compound | Product name (manufacturer) | Parts by mass |
| Particles | Particles | Cellulose acetate particles indicated in Table 3 | 10 |
| Component A | (Dimethicone/PEG-10/15) crosspolymer, dimethicone | KSG-210 (Shin-Etsu Chemical Co., Ltd.) | 3.5 |
| | PEG-9 polydimethylsiloxyethyl dimethicone | KF-6028 (Shin-Etsu Chemical Co., Ltd.) | 2 |
| | Dimethicone | KF-7312K (Shin-Etsu Chemical Co., Ltd.) | 5 |
| | Isononyl isononanoate | KAK99 (KOKYU ALCOHOL KOGYO CO., LTD.) | 4.5 |
| | Octyl methoxycinnamate | NOMCORT TAB (The Nisshin OilliO Group, Ltd.) | 10 |
| | Quaternium-18 Hectorite | SUMECTON SAN (KUNIMINE INDUSTRIES CO., LTD.) | 1.2 |
| | (Dimethicone/vinyldimethicone) crosspolymer, dimethicone | KSG-16 (Shin-Etsu Chemical Co., Ltd.) | 5 |
| | Cyclomethicone | DOESIL SH245 Fluid (Dow Toray Co., Ltd.) | 25 |
| Component B | 1,3-Butylene glycol | HAISUGARCANE BG (KOKYU ALCOHOL KOGYO CO., LTD.) | 5 |
| | Sodium citrate | Trisodium citrate (Jungbunzlauer International AG) | 2 |
| | Preservative | POTIPHEN HD (Ashland Japan) | 0.3 |
| | Purified water | | 26.5 |
| | | Total | 100 |

Lipstick Base

According to the formulation indicated in Table 2-8, a component B is heated to 60° C. and mixed. Thereto, particles are dispersed and the component A is added, and the resulting mixture is mixed by heating and melting in a microwave oven and cooled. The resulting product is set in a lipstick casing to obtain a lipstick base.

TABLE 2-8

| Lipstick base | | | |
|---|---|---|---|
| Formulation | Compound | Product name (manufacturer) | Parts by mass |
| Particles | Particles | Cellulose acetate particles indicated in Table 3 | 10 |
| Component A | Ceresin | CERESIN #810 (NIKKO RICA CORPORATION) | 4.27 |
| | Microcrystalline wax | Purified microcrystalline wax (NIKKO RICA CORPORATION) | 1.55 |
| | Candelilla wax | Purified candelilla wax No. 1 (Nippon Wax Co., Ltd.) | 5.03 |
| | Paraffin | Purified paraffin wax (NIKKO RICA CORPORATION) | 3.07 |
| Component B | Diisostearyl malate | Neosolue-DiSM (NIPPON FINE CHEMICAL CO., LTD) | 17.95 |
| | Dipentaerythrite fatty acid ester | COSMOL 168EV (The Nisshin OilliO Group, Ltd.) | 6.22 |
| | Adsorption purified lanoline | SUPER STEROL LIQUID (Croda Japan) | 2.52 |
| | Liquid lanolin acetate | ACELAN SP (Croda Japan) | 13.34 |
| | Ethyl hexyl glyceryl | GLYMOIST (NOF CORPORATION) | 19.02 |
| | Liquid paraffin | HYDROBRITE 380 PO (Sonneborn) | 7.28 |
| | Isotridecyl isononanoate | KAK139 (KOKYU ALCOHOL KOGYO CO., LTD.) | 3.21 |
| | Polyglyceryl-2 triisostearate | EMALEX TISG-2 (NIHON EMULSION Co., Ltd.) | 4.01 |
| | Methylphenylpolysiloxane | BELSIL PDM 20 (Wacker Asahikasei Silicone Co., Ltd.) | 2.41 |
| | Methylparaben | Nipagin M (Clariant Japan) | 0.07 |
| | Tocopherol | Tocopherol 100 (The Nisshin OilliO Group, Ltd.) | 0.05 |
| | | Total | 100 |

Body Powder

The formulation indicated in Table 2-9 is mixed in a laboratory mixer to obtain a body powder.

TABLE 2-9

| Body Powder | | | |
|---|---|---|---|
| Formulation | Compound | Product name (manufacturer) | Parts by mass |
| Particles | Particles | Cellulose acetate particles indicated in Table 3 | 10 |
| Formulation other than particles | Talc | Talc CT-25 (YAMAGUCHI MICA CO., LTD.) | 89.7 |
| | Fragrance | Bisabolol rac. (BASF Japan) | 0.3 |
| | | Total | 100 |

Solid Powder Eyeshadow

According to the formulation indicated in Table 2-10, particles and powders are mixed, the binder is evenly melted, the resulting solution is added to the powder mixture, and the resulting mixture is further mixed and compacted to obtain a solid powder eyeshadow.

TABLE 2-10

| Solid powder eyeshadow | | | |
|---|---|---|---|
| Formulation | Compound | Product name (manufacturer) | Parts by mass |
| Particles | Particles | Cellulose acetate particles indicated in Table 3 | 51 |
| Formulation other than particles | Mica | Talc CT-25 (YAMAGUCHI MICA CO., LTD.) | 15 |
| | Sericite | Sericite FSE (SANSHIN MINING IND. CO., LTD.) | 5 |
| | Pigment | Unipure Blue LC 621 (Sensient Technologies Japan) | 15 |
| | Pearl pigment | TWINCLEPEARL (NIHON KOKEN KOGYO CO., LTD.) | 10 |
| Binder | Methylpolysiloxane | BELSIL DM 10 (Wacker Asahikasei Silicone Co., Ltd.) | 2 |
| | Sorbitan sesquioleate | EMALEX SPO-150 (NIHON EMULSION Co., Ltd.) | 2 |
| | | Total | 100 |

Evaluation

The softness and the coarse feel of the cellulose acetate particles of each Example and the obtained cosmetic items are evaluated as follows.

A 5 g sample of each of the cellulose acetate particles and the cosmetic items is placed on and spread over the back of a hand of ten female monitors, and rated in the scale of 0 to 10 with 10 being the best and 0 being the worst regarding the softness and the coarse feel. Then the points given by the ten testers are arithmetically averaged and evaluated.

This task is performed on the untreated cellulose acetate particles and cosmetic items (in the tables, indicated as "Initial") and on the cellulose acetate particles and cosmetic items (in the tables, indicated as "Storage") that have been stored still at room temperature for 3 months.

TABLE 3-1

| | Particle | Cellulose acetate particles | | | | Liquid foundation | | | | Milky lotion | |
|---|---|---|---|---|---|---|---|---|---|---|---|
| | | Softness | | Coarse Feel | | Softness | | Coarse Feel | | Softness | |
| | No. | Initial | Storage | Initial | Storage | Initial | Storage | Initial | Storage | Initial | Storage |
| Example 1 | PTC-1 | 9 | 8 | 9 | 8 | 10 | 9 | 10 | 9 | 10 | 9 |
| Example 2 | PTC-2 | 8 | 8 | 8 | 8 | 9 | 9 | 9 | 9 | 9 | 9 |
| Example 3 | PTC-3 | 9 | 7 | 9 | 7 | 10 | 8 | 10 | 8 | 10 | 8 |
| Example 4 | PTC-4 | 6 | 5 | 6 | 5 | 8 | 7 | 8 | 7 | 8 | 7 |
| Example 5 | PTC-5 | 5 | 5 | 5 | 5 | 7 | 7 | 7 | 7 | 7 | 7 |
| Example 6 | PTC-6 | 5 | 5 | 6 | 5 | 5 | 5 | 6 | 5 | 5 | 5 |
| Example 7 | PTC-7 | 6 | 5 | 6 | 5 | 8 | 7 | 6 | 7 | 8 | 7 |
| Example 8 | PTC-8 | 7 | 5 | 7 | 6 | 9 | 7 | 9 | 7 | 9 | 7 |
| Example 9 | PTC-9 | 7 | 5 | 7 | 5 | 8 | 6 | 8 | 6 | 8 | 6 |
| Example 10 | PTC-10 | 6 | 5 | 4 | 4 | 7 | 6 | 5 | 5 | 7 | 6 |
| Example 11 | PTC-11 | 8 | 7 | 8 | 7 | 9 | 8 | 9 | 8 | 9 | 8 |
| Example 12 | PTC-12 | 8 | 7 | 8 | 7 | 9 | 8 | 9 | 8 | 9 | 8 |
| Example 13 | PTC-13 | 8 | 7 | 8 | 7 | 9 | 8 | 9 | 8 | 9 | 8 |
| Example 14 | PTC-14 | 8 | 7 | 8 | 7 | 9 | 8 | 9 | 8 | 9 | 8 |
| Example 15 | PTC-15 | 8 | 7 | 8 | 7 | 9 | 8 | 9 | 8 | 9 | 8 |
| Example 16 | PTC-16 | 8 | 7 | 8 | 7 | 9 | 8 | 9 | 8 | 9 | 8 |
| Example 17 | PTC-17 | 8 | 7 | 8 | 7 | 9 | 8 | 9 | 8 | 9 | 8 |
| Example 18 | PTC-18 | 8 | 7 | 8 | 7 | 9 | 8 | 9 | 8 | 9 | 8 |
| Example 19 | PTC-19 | 8 | 7 | 8 | 7 | 9 | 8 | 9 | 8 | 9 | 8 |
| Example 20 | PTC-20 | 9 | 8 | 9 | 8 | 10 | 9 | 10 | 9 | 10 | 9 |
| Example 21 | PTC-21 | 7 | 6 | 7 | 6 | 8 | 7 | 8 | 7 | 8 | 7 |
| Example 22 | PTC-22 | 6 | 4 | 6 | 4 | 8 | 5 | 8 | 5 | 8 | 5 |
| Comparative Example 1 | PTC-23 | 3 | 3 | 3 | 3 | 5 | 5 | 5 | 5 | 5 | 5 |
| Comparative Example 2 | PTC-24 | 6 | 4 | 6 | 4 | 7 | 5 | 7 | 5 | 7 | 5 |
| Comparative Example 3 | PTC-25 | 6 | 1 | 6 | 1 | 8 | 3 | 8 | 3 | 8 | 3 |
| Comparative Example 4 | PTC-26 | 6 | 1 | 6 | 1 | 8 | 3 | 8 | 3 | 8 | 3 |

| | Milky lotion | | Loose powder | | | | Powder foundation | | | |
|---|---|---|---|---|---|---|---|---|---|---|
| | Coarse Feel | | Softness | | Coarse Feel | | Softness | | Coarse Feel | |
| | Initial | Storage | Initial | Storage | Initial | Storage | Initial | Storage | Initial | Storage |
| Example 1 | 10 | 9 | 9 | 8 | 9 | 8 | 10 | 9 | 10 | 9 |
| Example 2 | 9 | 9 | 8 | 8 | 8 | 8 | 9 | 9 | 9 | 9 |
| Example 3 | 10 | 8 | 9 | 7 | 9 | 7 | 10 | 8 | 10 | 8 |

TABLE 3-1-continued

| | | | | | | | | | | |
|---|---|---|---|---|---|---|---|---|---|---|
| Example 4 | 8 | 7 | 7 | 6 | 7 | 6 | 8 | 7 | 8 | 7 |
| Example 5 | 7 | 7 | 6 | 6 | 6 | 6 | 7 | 7 | 7 | 7 |
| Example 6 | 6 | 5 | 4 | 4 | 5 | 4 | 5 | 5 | 6 | 5 |
| Example 7 | 8 | 7 | 7 | 6 | 8 | 6 | 8 | 7 | 7 | 7 |
| Example 8 | 9 | 7 | 8 | 6 | 8 | 6 | 9 | 7 | 9 | 7 |
| Example 9 | 8 | 6 | 8 | 6 | 8 | 6 | 8 | 6 | 8 | 6 |
| Example 10 | 5 | 5 | 7 | 6 | 5 | 5 | 7 | 6 | 5 | 5 |
| Example 11 | 9 | 8 | 8 | 7 | 8 | 7 | 9 | 8 | 9 | 8 |
| Example 12 | 9 | 8 | 8 | 7 | 8 | 7 | 9 | 8 | 9 | 8 |
| Example 13 | 9 | 8 | 8 | 7 | 8 | 7 | 9 | 8 | 9 | 8 |
| Example 14 | 9 | 8 | 8 | 7 | 8 | 7 | 9 | 8 | 9 | 8 |
| Example 15 | 9 | 8 | 8 | 7 | 8 | 7 | 9 | 8 | 9 | 8 |
| Example 16 | 9 | 8 | 8 | 7 | 8 | 7 | 9 | 8 | 9 | 8 |
| Example 17 | 9 | 8 | 8 | 7 | 8 | 7 | 9 | 8 | 9 | 8 |
| Example 18 | 9 | 8 | 8 | 7 | 8 | 7 | 9 | 8 | 9 | 8 |
| Example 19 | 9 | 8 | 8 | 7 | 8 | 7 | 9 | 8 | 9 | 8 |
| Example 20 | 10 | 9 | 9 | 8 | 9 | 8 | 10 | 9 | 10 | 9 |
| Example 21 | 8 | 7 | 7 | 6 | 7 | 6 | 8 | 7 | 8 | 7 |
| Example 22 | 8 | 5 | 7 | 4 | 7 | 4 | 8 | 5 | 8 | 5 |
| Comparative Example 1 | 5 | 5 | 4 | 4 | 4 | 4 | 5 | 5 | 5 | 5 |
| Comparative Example 2 | 7 | 5 | 6 | 4 | 6 | 4 | 7 | 5 | 7 | 5 |
| Comparative Example 3 | 8 | 3 | 7 | 2 | 7 | 2 | 8 | 3 | 8 | 3 |
| Comparative Example 4 | 8 | 3 | 7 | 2 | 7 | 2 | 8 | 3 | 8 | 3 |

TABLE 3-2

| | Sunscreen cream | | | | All-in-one gel | | | | Makeup base | | | |
|---|---|---|---|---|---|---|---|---|---|---|---|---|
| | Softness | | Coarse Feel | | Softness | | Coarse Feel | | Softness | | Coarse Feel | |
| | Initial | Storage | Initial | Storage | Initial | Storage | Initial | Storage | Initial | Storage | Initial | Storage |
| Example 1 | 10 | 9 | 10 | 9 | 10 | 9 | 10 | 9 | 10 | 9 | 10 | 9 |
| Example 2 | 9 | 9 | 9 | 9 | 9 | 9 | 9 | 9 | 9 | 9 | 9 | 9 |
| Example 3 | 10 | 8 | 10 | 8 | 10 | 8 | 10 | 8 | 10 | 8 | 10 | 8 |
| Example 4 | 8 | 7 | 8 | 7 | 8 | 7 | 8 | 7 | 8 | 7 | 8 | 7 |
| Example 5 | 7 | 7 | 7 | 7 | 7 | 7 | 7 | 7 | 7 | 7 | 7 | 7 |
| Example 6 | 5 | 5 | 6 | 5 | 5 | 5 | 6 | 5 | 5 | 5 | 6 | 5 |
| Example 7 | 8 | 7 | 8 | 7 | 8 | 7 | 8 | 7 | 8 | 7 | 8 | 7 |
| Example 8 | 9 | 7 | 9 | 7 | 9 | 7 | 9 | 7 | 9 | 7 | 9 | 7 |
| Example 9 | 8 | 6 | 8 | 6 | 8 | 6 | 8 | 6 | 8 | 6 | 8 | 6 |
| Example 10 | 7 | 6 | 5 | 5 | 7 | 6 | 5 | 5 | 7 | 6 | 5 | 5 |
| Example 11 | 9 | 8 | 9 | 8 | 9 | 8 | 9 | 8 | 9 | 8 | 9 | 8 |
| Example 12 | 9 | 8 | 9 | 8 | 9 | 8 | 9 | 8 | 9 | 8 | 9 | 8 |
| Example 13 | 9 | 8 | 9 | 8 | 9 | 8 | 9 | 8 | 9 | 8 | 9 | 8 |
| Example 14 | 9 | 8 | 9 | 8 | 9 | 8 | 9 | 8 | 9 | 8 | 9 | 8 |
| Example 15 | 9 | 8 | 9 | 8 | 9 | 8 | 9 | 8 | 9 | 8 | 9 | 8 |
| Example 16 | 9 | 8 | 9 | 8 | 9 | 8 | 9 | 8 | 9 | 8 | 9 | 8 |
| Example 17 | 9 | 8 | 9 | 8 | 9 | 8 | 9 | 8 | 9 | 8 | 9 | 8 |
| Example 18 | 9 | 8 | 9 | 8 | 9 | 8 | 9 | 8 | 9 | 8 | 9 | 8 |
| Example 19 | 9 | 8 | 9 | 8 | 9 | 8 | 9 | 8 | 9 | 8 | 9 | 8 |
| Example 20 | 10 | 9 | 10 | 9 | 10 | 9 | 10 | 9 | 10 | 9 | 10 | 9 |
| Example 21 | 8 | 7 | 8 | 7 | 8 | 7 | 8 | 7 | 8 | 7 | 8 | 7 |
| Example 22 | 8 | 5 | 8 | 5 | 8 | 5 | 8 | 5 | 8 | 5 | 8 | 5 |
| Comparative Example 1 | 5 | 5 | 5 | 5 | 5 | 5 | 5 | 5 | 5 | 5 | 5 | 5 |
| Comparative Example 2 | 7 | 5 | 7 | 5 | 7 | 5 | 7 | 5 | 7 | 5 | 7 | 5 |
| Comparative Example 3 | 8 | 3 | 8 | 3 | 8 | 3 | 8 | 3 | 8 | 3 | 8 | 3 |
| Comparative Example 4 | 8 | 3 | 8 | 3 | 8 | 3 | 8 | 3 | 8 | 3 | 8 | 3 |

| | Lipstick base | | | | Body powder | | | | Solid powder eyeshadow | | | |
|---|---|---|---|---|---|---|---|---|---|---|---|---|
| | Softness | | Coarse Feel | | Softness | | Coarse Feel | | Softness | | Coarse Feel | |
| | Initial | Storage | Initial | Storage | Initial | Storage | Initial | Storage | Initial | Storage | Initial | Storage |
| Example 1 | 10 | 9 | 10 | 9 | 9 | 8 | 9 | 8 | 10 | 9 | 10 | 9 |
| Example 2 | 9 | 9 | 9 | 9 | 8 | 8 | 8 | 8 | 9 | 9 | 9 | 9 |
| Example 3 | 10 | 8 | 10 | 8 | 9 | 7 | 9 | 7 | 10 | 8 | 10 | 8 |
| Example 4 | 8 | 7 | 8 | 7 | 7 | 6 | 7 | 6 | 8 | 7 | 8 | 7 |

TABLE 3-2-continued

| | | | | | | | | | | | | |
|---|---|---|---|---|---|---|---|---|---|---|---|---|
| Example 5 | 7 | 7 | 7 | 7 | 6 | 6 | 6 | 6 | 7 | 7 | 7 | 7 |
| Example 6 | 5 | 5 | 6 | 5 | 4 | 4 | 5 | 4 | 5 | 5 | 6 | 5 |
| Example 7 | 8 | 7 | 8 | 7 | 7 | 6 | 8 | 6 | 8 | 7 | 7 | 7 |
| Example 8 | 9 | 7 | 9 | 7 | 8 | 6 | 8 | 6 | 9 | 7 | 9 | 7 |
| Example 9 | 8 | 6 | 8 | 6 | 8 | 6 | 8 | 6 | 8 | 6 | 8 | 6 |
| Example 10 | 7 | 6 | 5 | 5 | 7 | 6 | 5 | 5 | 7 | 6 | 5 | 5 |
| Example 11 | 9 | 8 | 9 | 8 | 8 | 7 | 8 | 7 | 9 | 8 | 9 | 8 |
| Example 12 | 9 | 8 | 9 | 8 | 8 | 7 | 8 | 7 | 9 | 8 | 9 | 8 |
| Example 13 | 9 | 8 | 9 | 8 | 8 | 7 | 8 | 7 | 9 | 8 | 9 | 8 |
| Example 14 | 9 | 8 | 9 | 8 | 8 | 7 | 8 | 7 | 9 | 8 | 9 | 8 |
| Example 15 | 9 | 8 | 9 | 8 | 8 | 7 | 8 | 7 | 9 | 8 | 9 | 8 |
| Example 16 | 9 | 8 | 9 | 8 | 8 | 7 | 8 | 7 | 9 | 8 | 9 | 8 |
| Example 17 | 9 | 8 | 9 | 8 | 8 | 7 | 8 | 7 | 9 | 8 | 9 | 8 |
| Example 18 | 9 | 8 | 9 | 8 | 8 | 7 | 8 | 7 | 9 | 8 | 9 | 8 |
| Example 19 | 9 | 8 | 9 | 8 | 8 | 7 | 8 | 7 | 9 | 8 | 9 | 8 |
| Example 20 | 10 | 9 | 10 | 9 | 9 | 8 | 9 | 8 | 10 | 9 | 10 | 9 |
| Example 21 | 8 | 7 | 8 | 7 | 7 | 6 | 7 | 6 | 8 | 7 | 8 | 7 |
| Example 22 | 8 | 5 | 8 | 5 | 7 | 4 | 7 | 4 | 8 | 5 | 8 | 5 |
| Comparative Example 1 | 5 | 5 | 5 | 5 | 4 | 4 | 4 | 4 | 5 | 5 | 5 | 5 |
| Comparative Example 2 | 7 | 5 | 7 | 5 | 6 | 4 | 6 | 4 | 7 | 5 | 7 | 5 |
| Comparative Example 3 | 8 | 3 | 8 | 3 | 7 | 2 | 7 | 2 | 8 | 3 | 8 | 3 |
| Comparative Example 4 | 8 | 3 | 8 | 3 | 7 | 2 | 7 | 2 | 8 | 3 | 8 | 3 |

The results described above indicate that, compared to cellulose acetate of Comparative Examples, the cellulose acetate particles of Examples remain soft and give less coarse feel even after long-term storage.

The foregoing description of the exemplary embodiments of the present disclosure has been provided for the purposes of illustration and description. It is not intended to be exhaustive or to limit the disclosure to the precise forms disclosed. Obviously, many modifications and variations will be apparent to practitioners skilled in the art. The embodiments were chosen and described in order to best explain the principles of the disclosure and its practical applications, thereby enabling others skilled in the art to understand the disclosure for various embodiments and with the various modifications as are suited to the particular use contemplated. It is intended that the scope of the disclosure be defined by the following claims and their equivalents.

APPENDIX (((1)))

Cellulose acetate particles comprising cellulose acetate as a main component, wherein a total degree of acyl substitution of the cellulose acetate is 0.05 or more and less than 0.70.

(((2)))

The cellulose acetate particles described in (((1))), wherein acyl groups in the cellulose acetate are only acetyl groups.

(((3)))

The cellulose acetate particles described in (((1))) or (((2))), wherein the total degree of acyl substitution of the cellulose acetate is 0.15 or more and 0.6 or less.

(((4)))

The cellulose acetate particles described in (((3))), wherein the total degree of acyl substitution of the cellulose acetate is 0.25 or more and 0.5 or less.

(((5)))

The cellulose acetate particles described in any one of (((1))) to (((4))), wherein the cellulose acetate particles have a volume-average particle diameter of more than 1 μm and 100 μm or less.

(((6)))

The cellulose acetate particles described in (((5))), wherein the cellulose acetate particles have a volume-average particle diameter of 3 μm or more and 80 μm or less.

(((7)))

The cellulose acetate particles described in any one of (((1))) to (((6))), comprising:

a base particle that contains the cellulose acetate as a main component, and a coating layer coating the base particle and containing at least one coating material selected from the group consisting of fatty acids, fatty acid metal salts, amino acid compounds, lipid compounds, silicone compounds, fluorine compounds, and ceramide compounds.

(((8)))

The cellulose acetate particles described in (((7))), further comprising:

an intermediate layer between the base particle and the coating layer, wherein the intermediate layer contains at least one intermediate material selected from the group consisting of polyamine compounds, polyquaterniums, polysaccharide compounds, and polyacrylic acids.

(((9)))

The cellulose acetate particles described in any one of (((1))) to (((7))), further comprising inorganic particles that are externally added.

What is claimed is:

1. Cellulose acetate particles comprising:

a base particle that contains cellulose acetate as a main component, a coating layer coating the base particle and containing at least one coating material selected from the group consisting of fatty acids, fatty acid metal salts, amino acid compounds, lipid compounds, silicone compounds, fluorine compounds, and ceramide compounds, and an intermediate layer between the base particle and the coating layer, wherein a total degree of acyl substitution of the cellulose acetate is 0.05 or more and less than 0.70, and the intermediate layer contains at least one intermediate material selected from the group consisting of polyamine compounds, polyquaterniums, polysaccharide compounds, and polyacrylic acids.

2. The cellulose acetate particles according to claim 1, wherein acyl groups in the cellulose acetate are only acetyl groups.

3. The cellulose acetate particles according to claim 1, wherein the total degree of acyl substitution of the cellulose acetate is 0.15 or more and 0.6 or less.

4. The cellulose acetate particles according to claim 2, wherein the total degree of acyl substitution of the cellulose acetate is 0.15 or more and 0.6 or less.

5. The cellulose acetate particles according to claim 3, wherein the total degree of acyl substitution of the cellulose acetate is 0.25 or more and 0.5 or less.

6. The cellulose acetate particles according to claim 4, wherein the total degree of acyl substitution of the cellulose acetate is 0.25 or more and 0.5 or less.

7. The cellulose acetate particles according to claim 1, wherein the cellulose acetate particles have a volume-average particle diameter of more than 1 μm and 100 μm or less.

8. The cellulose acetate particles according to claim 2, wherein the cellulose acetate particles have a volume-average particle diameter of more than 1 μm and 100 μm or less.

9. The cellulose acetate particles according to claim 7, wherein the cellulose acetate particles have a volume-average particle diameter of 3 μm or more and 80 μm or less.

10. The cellulose acetate particles according to claim 8, wherein the cellulose acetate particles have a volume-average particle diameter of 3 μm or more and 80 μm or less.

11. The cellulose acetate particles according to claim 1, further comprising inorganic particles that are externally added.

12. The cellulose acetate particles according to claim 2, further comprising inorganic particles that are externally added.

* * * * *